United States Patent
Stemmler et al.

(10) Patent No.: US 9,434,671 B2
(45) Date of Patent: *Sep. 6, 2016

(54) NITROGEN MONOXIDE AS CIS/TRANS ISOMERIZATION CATALYSTS FOR UNSATURATED COMPOUNDS

(71) Applicant: DSM IP ASSETS B.V., Heerlen (NL)

(72) Inventors: René Tobias Stemmler, Kaiseraugst (CH); Nadine Greiner, Kaiseraugst (CH); Angela Wildermann, Kaiseraugst (CH)

(73) Assignee: DSM IP ASSETS B.V., Heerlen (NL)

(*) Notice: Subject to any disclaimer, the term of this patent is extended or adjusted under 35 U.S.C. 154(b) by 0 days.

This patent is subject to a terminal disclaimer.

(21) Appl. No.: 14/652,286

(22) PCT Filed: Dec. 18, 2013

(86) PCT No.: PCT/IB2013/061083
§ 371 (c)(1),
(2) Date: Jun. 15, 2015

(87) PCT Pub. No.: WO2014/097172
PCT Pub. Date: Jun. 26, 2014

(65) Prior Publication Data
US 2015/0321987 A1 Nov. 12, 2015

(30) Foreign Application Priority Data

Dec. 18, 2012 (EP) .................................... 12197803

(51) Int. Cl.
| | | |
|---|---|---|
| *C07C 45/67* | (2006.01) | |
| *C07C 29/56* | (2006.01) | |
| *C07C 33/02* | (2006.01) | |
| *C07C 43/313* | (2006.01) | |
| *C07C 49/203* | (2006.01) | |

(52) U.S. Cl.
CPC ............ *C07C 43/313* (2013.01); *C07C 29/56* (2013.01); *C07C 33/02* (2013.01); *C07C 45/67* (2013.01); *C07C 49/203* (2013.01); *C07B 2200/09* (2013.01)

(58) Field of Classification Search
CPC ........ C07C 45/67; C07C 29/56; C07C 33/02
USPC ........................................ 568/384, 417, 906
See application file for complete search history.

(56) References Cited

U.S. PATENT DOCUMENTS 5,908,957 A * 6/1999 Wildermann ........... C07B 37/08
560/128

FOREIGN PATENT DOCUMENTS

| | | |
|---|---|---|
| CH | 620 891 | 12/1980 |
| CN | 1201787 | 12/1998 |
| EP | 0 858 986 | 8/1998 |
| EP | 1 167 331 | 1/2002 |

OTHER PUBLICATIONS

Chew et al. Indentification of the bchP Gene, Encoding Geranylgeranyl Reductase in Chlorobaculum tepidum. Journal of Bacteriology, vol. 190 (2), 2008, p. 747-749.*
Chow et al. Studies on Taxadiene Synthase: Interception of the Cyclization Cascade at the Isocembrane Stage with GGPP Analogues. Journal of Organic Chemistry, 2005, vol. 70, p. 9997-10003.*
International Search Report for PCT/IB2013/061083 mailed Feb. 26, 2014, three pages.
"Palladium mediated C—H activation in the field of terpenoids: synthesis of rostratone", Jose Justicia et al., Tetrahedron Letters 45 (2004) 4293-4296.
"Stereochemistry of Aplidiasphingosine as Proposed by the Asymmetric Synthesis and 13C-NMR Study of Sphingosine Relatives", Kenji Mori et al., Tetrahedron Letters, vol. 22, No. 44, pp. 4433-4436 (1981).
Official Action, CN Appln. No. 201380065896.5 (Mar. 17, 2016).

* cited by examiner

*Primary Examiner* — Sikarl Witherspoon
(74) *Attorney, Agent, or Firm* — Nixon & Vanderhye P.C.

(57) ABSTRACT

The present invention relates to a process of a cis/trans isomerization of an unsaturated compound A being selected from the group consisting of unsaturated ketones, unsaturated ketals, unsaturated aldehydes, unsaturated acetals, unsaturated carboxylic acids, esters of an unsaturated carboxylic acid and amides of an unsaturated carboxylic acid using nitrogen monoxide as cis/trans isomerization catalyst. It has been observed that the isomerization is very efficient and fast.

17 Claims, 4 Drawing Sheets

NITROGEN MONOXIDE AS CIS/TRANS ISOMERIZATION CATALYSTS FOR UNSATURATED COMPOUNDS

This application is the U.S. national phase of International Application No. PCT/IB2013/061083 filed 18 Dec. 2013 which designated the U.S. and claims priority to EP 12197803.5 filed 18 Dec. 2012, the entire contents of each of which are hereby incorporated by reference.

TECHNICAL FIELD

The present invention relates to the cis/trans isomerization of unsaturated compounds.

BACKGROUND OF THE INVENTION

Unsaturated compounds have carbon-carbon double bonds. These compounds exist in either the cis or the trans configuration. Specifically unsaturated compounds containing functional groups having C=O are technically very important and have different properties depending on which double bond isomer (cis or trans) is present in the corresponding compound. These compounds are particularly important for the fields of flavours and fragrances, pharmaceutical compositions and the synthesis of vitamins, particularly of vitamin K1 as well as tocopherols. The isomers particularly differ in odour as well as in their behaviour towards asymmetric additions to the respective carbon-carbon double bond.

It is known that carbon-carbon double bonds can be isomerized. EP 0 858 986 A1 discloses a process to isomerize vitamin A compounds having a system of polyconjugated carbon-carbon double bonds (—C=C—C=C—C=C—C=C—C=C—) by nitrogen monoxide. It is, however, known that compounds having isolated (non-conjugated) double bonds strongly differ in their behavior, particularly reactivity, compared to behave strongly different than compounds having polyconjugated carbon-carbon bonds.

SUMMARY OF THE INVENTION

Therefore, the problem to be solved by the present invention is to offer a process of isomerization and an isomerization catalyst which is very efficient, respectively, for compounds being selected from the group consisting of unsaturated ketones, unsaturated ketals, unsaturated aldehydes, unsaturated acetals, unsaturated carboxylic acids, esters of an unsaturated carboxylic acid, amides of an unsaturated carboxylic acid and unsaturated alcohols.

Surprisingly, it has been found that a process according to the claims 1, 10 as well as the composition according to claim 12 is able to solve this problem. It has been found that nitrogen monoxide is particularly suitable for the isomerization of the above mentioned compounds. It isomerizes the carbon-carbon double bond of these compounds very efficiently. Due to the process of the invention it has become possible to have transformed essentially all of the undesired isomer into the desired isomer. This is not only possible in the case of a pure isomer but also in case of a mixture.

Further aspects of the invention are subject of further independent claims. Particularly preferred embodiments are subject of dependent claims.

DETAILED DESCRIPTION OF THE INVENTION

In a first aspect the present invention relates to a process of a cis/trans isomerization of an unsaturated compound A being selected from the group consisting of unsaturated ketones, unsaturated ketals, unsaturated aldehydes, unsaturated acetals, unsaturated carboxylic acids, esters of an unsaturated carboxylic acid, amides of an unsaturated carboxylic acid and unsaturated alcohols comprising the steps
  a) providing a cis or a trans isomer of a unsaturated compound A;
  b) adding nitrogen monoxide to the cis or trans isomer of the unsaturated compound A of step a);
  c) heating the mixture of nitrogen monoxide and cis or trans isomer of the unsaturated compound A to a temperature of between 10° C. and the boiling point of the unsaturated compound A, particularly between 20° C. and the boiling point of the unsaturated compound A;

leading to a mixture of cis/trans isomers of the unsaturated compound A.

The term "independently from each other" in this document means, in the context of substituents, moieties, or groups, that identically designated substituents, moieties, or groups can occur simultaneously with a different meaning in the same molecule.

A "$C_{x-y}$-alkyl" group is an alkyl group comprising x to y carbon atoms, i.e., for example, a $C_{1-3}$-alkyl group is an alkyl group comprising 1 to 3 carbon atoms. The alkyl group can be linear or branched. For example —CH(CH$_3$)—CH$_2$—CH$_3$ is considered as a $C_4$-alkyl group.

A "$C_{x-y}$-alkylene" group is an alkylene group comprising x to y carbon atoms, i.e., for example $C_2$-$C_6$ alkylene group is an alkyl group comprising 2 to 6 carbon atoms. The alkylene group can be linear or branched. For example the group —CH(CH$_3$)—CH$_2$— is considered as a $C_3$-alkylene group.

A "phenolic alcohol" means in this document an alcohol which has a hydroxyl group which is bound directly to an aromatic group.

The term "stereogenic centre" as used in this document is an atom, bearing groups such that interchanging of any two of the groups leads to a stereoisomer. Stereoisomers are isomeric molecules that have the same molecular formula and sequence of bonded atoms (constitution), but that differ in the three-dimensional orientations of their atoms in space.

The configuration at a stereogenic centre is defined to be either R or S. The R/S-concept and rules for the determination of the absolute configuration in stereochemistry is known to the person skilled in the art.

In the present document a carbon-carbon double bond is defined as being "prochiral" if addition of molecular hydrogen to said carbon-carbon double bond leads to the formation of a stereogenic carbon centre.

Cis/trans isomers are configurational isomers having different orientation at the double bond. In this document the term "cis" is equivalently used for "Z" and vice versa as well as "trans" for "E" and vice versa. Therefore, for example the term "cis/trans isomerization catalyst" is equivalent to the term "E/Z isomerization catalyst".

A "cis/trans isomerization catalyst" is a catalyst which is able to isomerize a cis isomer (Z-isomer) to a cis/trans isomer mixture (E/Z isomer mixture) or to isomerize a trans isomer (E-isomer) to a cis/trans isomer (E/Z isomer mixture).

The terms "E/Z", "cis/trans" and "R/S" denote mixtures of E and Z, of cis and trans, and of R and S, respectively.

The term "isomerization" or "isomerize" is to be understood as being limited to cis/trans isomerization in the whole document.

An "equilibrium cis/trans ratio" is the ratio of a specific couple of cis and trans isomer which is achieved as a result of submitting either said cis or trans isomer to an isomerization using the process of this invention for an extended time, i.e. until no further change of the cis/trans ratio can be observed in time. Each pair of cis/trans isomers has a different equilibrium cis/trans ratio.

A "non-equilibrium cis/trans ratio" is any ratio of cis to trans isomer which differs from the "equilibrium cis/trans ratio".

An "unsaturated" compound, ketone, ketal, aldehyde, acetal, carboxylic acid, ester of an unsaturated carboxylic acid, amide of an unsaturated carboxylic acid or an unsaturated alcohol is defined as to be a ketone, aldehyde, ketal, aldehyde, acetal, carboxylic acid, ester of an unsaturated carboxylic acid, amide of an unsaturated carboxylic acid or an unsaturated alcohol which is olefinically unsaturated, i.e. that it has at least one carbon-carbon double bond in its chemical structure, however, has no polyconjugated carbon-carbon double bond, i.e. more than two conjugated carbon-carbon double bonds, and which preferably has at least one prochiral carbon-carbon double bond. Preferably the "unsaturated" compound has no conjugated carbon-carbon double bonds.

In case identical labels for symbols or groups are present in several formulae, in the present document, the definition of said group or symbol made in the context of one specific formula applies also to other formulae which comprises said same label.

In the present document any single dotted line represents the bond by which a substituent is bound to the rest of a molecule.

In the present document the boldface designations such as A or $I_{lbp}$ or $I_{hbp}$ are used in the present document only for and identification to improve readability.

Unsaturated Compound A

The unsaturated compound A, selected from the group consisting of unsaturated ketones, unsaturated ketals, unsaturated aldehydes, unsaturated acetals, unsaturated carboxylic acids, esters of an unsaturated carboxylic acid, amides of an unsaturated carboxylic acid and unsaturated alcohols, has at least one carbon-carbon double bond in its chemical structure and preferably has at least one prochiral carbon-carbon double bond.

It may have more than 1 prochiral carbon-carbon double bonds and/or 1 or more non-prochiral carbon-carbon double bond(s).

Preferably the unsaturated compound A is of formula (I-0A) or (I-0B) or (I-0C) or (I-0D) or (I-0E) or (I-0F)

$$R' \diagup\!\!\!\diagup Q' \quad (I\text{-}0A)$$

$$R' \diagup\!\!\!\diagup\!\!\!\diagup Q' \quad (I\text{-}0B)$$

$$R' \diagup\!\!\!\diagup Q' \quad (I\text{-}0C)$$

$$R' \diagup\!\!\!\diagup\!\!\!\diagup Q' \quad (I\text{-}0D)$$

$$R' \diagup\!\!\!\diagup Q' \quad (I\text{-}0E)$$

$$R' \diagup\!\!\!\diagup\!\!\!\diagup Q' \quad (I\text{-}0F)$$

wherein R' stands for a linear or a cycloaliphatic hydrocarbyl group which optionally contains additional carbon-carbon double bond(s), however, in the case of formula (I-0B) or (I-0D) or (I-0F) no conjugated double bonds and in the case of formula (I-0A) or (I-0C) or (I-0E) maximal one conjugated double bonds, and Q' stands for a group selected of the group consisting of wherein $R^0$ stands for a $C_1$-$C_4$-alkyl group, particularly for a methyl group; $Q^1$ and $Q^2$ stand for a $C_1$-$C_{10}$ alkyl group or a halogenated $C_1$-$C_{10}$ alkyl group; $C_1$-$C_4$-alkyl group or form together a $C_2$-$C_6$ alkylene group or a $C_6$-$C_8$ cycloalkylene group together;

R" stands for a $C_1$-$C_4$-alkyl group, particularly for a methyl or ethyl group; and R'" stands for H or a $C_1$-$C_4$-alkyl group, particularly for a methyl or ethyl group; and where a wavy line represents a carbon-carbon bond which is linked to the adjacent carbon-carbon double bond so as to have said carbon-carbon double bond either in the Z or in the E-configuration;

and wherein the double bond having dotted lines ( ===== ) in formula (I-0B) or (I-0D) or (I-0F) represent either a single carbon-carbon bond or a double carbon-carbon bond.

In one embodiment, the formula (I-0A) or (I-0C) has a group R' of the formula and is preferably a methylketone or a ketal thereof, preferably alpha-ionone, beta-ionone, gamma-ionone; alpha-iso-ionone, beta-iso-ionone, gamma-iso-ionone; Alpha-normal-methylionone, beta-normal-methylionone or gamma-normal-methylionone; or a ketal thereof It is preferred that the unsaturated compound A is an unsaturated ketone or unsaturated ketal or an unsaturated aldehyde or an unsaturated acetal or an unsaturated alcohol.

In one preferred embodiment the unsaturated compound A is an unsaturated ketone or ketal thereof or an unsaturated aldehyde or acetal thereof and has a carbon-carbon double bond in the γ,δ position relative to the carbonyl group.

In another preferred embodiment the unsaturated compound A is an unsaturated ketone or ketal thereof or an unsaturated aldehyde or acetal thereof and has a carbon-carbon double bond in the α,β position relative to the carbonyl group.

In a still another preferred embodiment the unsaturated compound A is an unsaturated ketone or ketal thereof or an unsaturated aldehyde or acetal thereof and has a carbon-carbon double bond in the α,β position relative to the carbonyl group and has a carbon-carbon double bond in the γ,δ position relative to the carbonyl group, however, no double bond in the ε,ζ position relative to the carbonyl group.

It is strongly preferred that that the unsaturated compound A is of formula (I) or (II) or (IID) or (IIE)

wherein Q stands for H or CH$_3$ and m and p stand independently from each other for a value of 0 to 3 with the proviso that the sum of m and p is 0 to 3; and where a wavy line represents a carbon-carbon bond which is linked to the adjacent carbon-carbon double bond so as to have said carbon-carbon double either in the Z or in the E-configuration and where the substructures in formula (I) and (II) and (IID) and (IIE) represented by S1 and s2 can be in any sequence;
and wherein the double bond having dotted lines (=====) in formula (I) and (II) and (IID) and (IIE) represent either a single carbon-carbon bond or a double carbon-carbon bond; and wherein ✧ represents a stereogenic centre.

The sum of m and p is preferably 0 to 2, particularly 0 or 1.

The unsaturated compound of formula (I) or (II) or (IID) or (IIE), hence, can be an individual substance or a mixture of different stereoisomers having different orientation at the stereogenic centres marked by ✧ or at the double bond to which the wavy bond is attached. It is preferred, however, that the unsaturated compound A of formula (I) or (II) is a single stereoisomer with specific configuration(s) at the stereogenic centres and double bonds. It is preferred that the configuration at the stereogenic centre(s) is the R-configuration. In case of p≥2, it is preferred that all the different stereogenic centres marked by ✧ have the same configuration, i.e. all the S-configuration or all the R-configuration, preferably all in the R-configuration.

Particularly suitable unsaturated compounds have the formula (II). Most preferably the unsaturated ketone or aldehyde is selected from the group consisting of 3,7-dimethylocta-2,6-dienal, 3,7-dimethyloct-2-enal, 6,10-dimethylundeca-3,5,9-trien-2-one, 6,10-dimethylundeca-5,9-dien-2-one, 6,10-dimethylundec-5-en-2-one, 6,10-dimethylundec-3-en-2-one, 6,10-dimethylundec-3,5-diene-2-one, (R)-6,10-dimethylundec-3-en-2-one, 6,10,14-trimethylpentadeca-5,9,13-trien-2-one, 6,10,14-trimethylpentadeca-5,9-dien-2-one, 6,10,14-trimethylpentadec-5-en-2-one and (R)-6,10,14-trimethylpentadec-5-en-2-one as well as all their possible E/Z-isomers.

Most preferably the unsaturated ketone or aldehyde is a ketone.

Further very suitable compound of formula (IID) and (IIE) are geraniol, nerol and farnesol.

Acetal/Ketal

It is, furthermore, preferred that the unsaturated compound A is a ketal or acetal of an unsaturated ketone or unsaturated aldehyde, particularly an acetal or a ketal of formula (I) or (II).

The formation of a ketal from a ketone, or of an acetal from an aldehyde, per se, is known to the person skilled in the art.

The ketal of an unsaturated ketone can be preferably formed from the above mentioned unsaturated ketone and an alcohol. The acetal of an unsaturated aldehyde can be formed from the above mentioned unsaturated aldehyde and an alcohol.

It is known to the person skilled in the art that there are alternative routes of synthesis for acetal or ketals. In principle, the ketal and acetals can also be formed by treating a ketone or an aldehyde with ortho-esters or by trans-ketalization such as disclosed for example in Pério et al., *Tetrahedron Letters* 1997, 38(45), 7867-7870, or in Lorette and Howard, *J. Org. Chem.* 1960, 25, 521-525, the entire content of both is hereby incorporated by reference.

Preferably the ketal or acetal is formed from the above mentioned unsaturated ketone or unsaturated aldehyde and an alcohol.

The alcohol used for the ketal or acetal formation can, principally, be any alcohol, i.e. the alcohol may comprise one or more hydroxyl groups. The alcohol may be a phenolic alcohol or an aliphatic or cycloaliphatic alcohol. Preferably, however, the alcohol has one hydroxyl group (=monol) or two hydroxyl groups (=diol).

In case the alcohol has one hydroxyl group, the alcohol is preferably an alcohol which has 1 to 12 carbon atoms. Particularly, the alcohol having one hydroxyl group is selected from the group consisting of methanol, ethanol, 1-propanol, 2-propanol, 1-butanol, 2-methyl-1-propanol, 2-butanol, pentane-1-ol, 3-methylbutane-1-ol, 2-methylbutane-1-ol, 2,2-dimethylpropan-1-ol, pentane-3-ol, pentane-2-ol, 3-methylbutane-2-ol, 2-methylbutan-2-ol, hexane-1-ol, hexane-2-ol, hexane-3-ol, 2-methyl-1-pentanol, 3-methyl-1-pentanol, 4-methyl-1-pentanol, 3-methyl-2-pentanol, 4-methyl-2-pentanol, 2-methyl-3-pentanol, 2,2-dimethyl-1-butanol, 2,3-dimethyl-1-butanol, 3,3-dimethyl-1-butanol, 3,3-dimethyl-2-butanol, 2-ethyl-1-butanol, and all structural isomers of heptanol, octanol and halogenated C$_1$-C$_8$-alkyl alcohols, particularly 2,2,2-trifluoroethanol. Particulalrly suitable are primary or secondary alcohols. Preferably primary alcohols are used as alcohols with one hydroxyl group.

Particularly methanol, ethanol, 1-propanol, 2-propanol, 1-butanol, 2-butanol or 2,2,2-trifluoroethanol, preferably methanol, ethanol, 1-propanol, 1-butanol or 2,2,2-trifluoroethanol, are used as alcohols with one hydroxyl group.

In another embodiment the alcohol is a diol. Preferably the diol is selected from the group consisting of ethane-1,2-diol, propane-1,2-diol, propane-1,3-diol, butane-1,4-diol, butane-1,3-diol, butane-1,2-diol, butane-2,3-diol, 2-methylpropane-1,2-diol, 2-methylpropane-1,3-diol, 2,2-dimethylpropane-1,3-diol, 1,2-dimethylpropane-1,3-diol, 3-methylpentane-2,4-diol and 2-(hydroxymethyl)cyclohexanol, benzene-1,2-diol and cyclohexane-1,2-diols. From two cyclohexane-1,2-diols the preferred stereoisomer is syn-cyclohexane-1,2-diol (=cis-cyclohexane-1,2-diol).

The two hydroxyl groups are in one embodiment bound to two adjacent carbon atoms, hence these diols are vicinal diols. Vicinal diols form a 5 membered ring in a ketal or acetal.

Particularly suitable alcohols are vicinal diols which are selected from the group consisting of ethane-1,2-diol, propane-1,2-diol, butane-1,2-diol, butane-2,3-diol, 2-methylpropane-1,2-diol, benzene-1,2-diol and syn-cyclohexane-1,2-diol, particularly ethane-1,2-diol.

Other particularly suitable are diols, in which the hydroxyl groups are separated by 3 carbon atoms, and, hence, form a very stable 6 membered ring in a ketal or acetal. Particularly suitable diols of this type are propane-1,3-diol, butane-1,3-diol, 2-methylpropane-1,3-diol, 2-methylbutane-1,3-diol, 2,2-dimethyl-propane-1,3-diol, 1,2-dimethylpropane-1,3-diol, 3-methylpentane-2,4-diol and 2-(hydroxymethyl)cyclohexanol.

Preferably primary alcohols are used as diols.

The reaction conditions and stoichiometry used for the acetal or ketal formation are known to the person skilled in the art. Particularly the acetal or ketal is formed under the influence of an acid.

The preferred ketal of an unsaturated ketone or the preferred acetal of an unsaturated aldehyde are of formula (XI) or (XII)

(XI)

(XII)

The groups and symbols in formula (XI) and (XII) have the same meaning as defined before in this document for formula (I) and (II).

$Q^1$ and $Q^2$ stand either individually both for a $C_1$-$C_{10}$ alkyl group or a halogenated $C_1$-$C_{10}$ alkyl group;
or form together a $C_2$-$C_6$ alkylene group or a $C_6$-$C_8$ cycloalkylene group.

$Q^1$ and $Q^2$ stand particularly for either a linear $C_1$-$C_{10}$ alkyl group or fluorinated linear $C_1$-$C_{10}$ alkyl group, preferably a linear $C_1$-$C_4$ alkyl group or a —$CH_2CF_3$ group or a group of formula in which $Q^3$, $Q^4$, $Q^5$ and $Q^6$ are independently from each other hydrogen atoms or methyl or ethyl groups.

Preferably the ketal or the acetal of formula (XI) or (XII) are (E)-2-(4,8-dimethylnona-3,7-dien-1-yl)-2,5,5-trimethyl-1,3-dioxane, (E)-2,6-dimethyl-10,10-bis(2,2,2-trifluoroethoxy)undeca-2,6-diene, (E)-2-(4,8-dimethylnon-3-en-1-yl)-2,5,5-trimethyl-1,3-dioxane, (E)-6,10-dimethyl-2,2-bis(2,2,2-trifluoroethoxy)undec-5-ene, (E)-2,5,5-trimethyl-2-(4,8,12-trimethyltridec-3-en-1-yl)-1,3-dioxane, (R,E)-2,5,5-trimethyl-2-(4,8,12-trimethyltridec-3-en-1-yl)-1,3-dioxane, (E)-6,10,14-tri-methyl-2,2-bis(2,2,2-trifluoroethoxy)pentadec-5-ene, (R,E)-6,10,14-trimethyl-2,2-bis(2,2,2-trifluoroethoxy)pentadec-5-ene, (Z)-2-(4,8-dimethylnona-3,7-dien-1-yl)-2,5,5-trimethyl-1,3-dioxane, (Z)-2,6-dimethyl-10,10-bis(2,2,2-trifluoroethoxy)un-deca-2,6-diene, (Z)-2-(4,8-dimethylnon-3-en-1-yl)-2,5,5-trimethyl-1,3-dioxane, (Z)-6,10-dimethyl-2,2-bis(2,2,2-trifluoroethoxy)undec-5-ene, (Z)-2,5,5-trimethyl-2-(4,8,12-trimethyltridec-3-en-1-yl)-1,3-dioxane, (R,Z)-2,5,5-trimethyl-2-(4,8,12-tri-methyltridec-3-en-1-yl)-1,3-dioxane, 2,5,5-trimethyl-2-((3E,7E)-4,8,12-trimethyltri-deca-3,7,11-trien-1-yl)-1,3-dioxane, (6E,10E)-2,6,10-trimethyl-14,14-bis(2,2,2-tri-fluoroethoxy)pentadeca-2,6,10-triene, 2,5,5-trimethyl-2-((3E,7E)-4,8,12-trimethyl-trideca-3,7-dien-1-yl)-1,3-dioxane, (5E,9E)-6,10,14-trimethyl-2,2-bis(2,2,2-trifluoro-ethoxy)pentadeca-5,9-diene, 2,5,5-trimethyl-2-((3Z,7E)-4,8,12-trimethyltrideca-3,7,11-trien-1-yl)-1,3-dioxane, 2,5,5-trimethyl-2-((3E,7Z)-4,8,12-trimethyltrideca-3,7,11-trien-1-yl)-1,3-dioxane, 2,5,5-trimethyl-2-((3Z,7Z)-4,8,12-trimethyltrideca-3,7,11-trien-1-yl)-1,3-dioxane, (6Z,10E)-2,6,10-trimethyl-14,14-bis(2,2,2-trifluoroethoxy)pentadeca-2,6,10-triene, (6E,10Z)-2,6,10-trimethyl-14,14-bis(2,2,2-trifluoroethoxy)pentadeca-2,6,10-triene, (6Z,10Z)-2,6,10-trimethyl-14,14-bis(2,2,2-trifluoroethoxy)pentadeca-2,6,10-triene, 2,5,5-trimethyl-2-((3Z,7E)-4,8,12-trimethyltrideca-3,7-dien-1-yl)-1,3-dioxane, 2,5,5-trimethyl-2-((3E,7Z)-4,8,12-trimethyltrideca-3,7-dien-1-yl)-1,3-dioxane, 2,5,5-trimethyl-2-((3Z,7Z)-4,8,12-trimethyltrideca-3,7-dien-1-yl)-1,3-dioxane, (5Z,9E)-6,10,14-trimethyl-2,2-bis(2,2,2-trifluoroethoxy)pentadeca-5,9-diene, (5E,9Z)-6,10,14-trimethyl-2,2-bis(2,2,2-trifluoroethoxy)pentadeca-5,9-diene, (5Z,9Z)-6,10,14-trimethyl-2,2-bis(2,2,2-trifluoroethoxy)pentadeca-5,9-diene, (E)-2-(2,6-dimethylhept-1-en-1-yl)-5,5-dimethyl-1,3-dioxane, (E)-3,7-dimethyl-1,1-bis(2,2,2-trifluoroethoxy)oct-2-ene, (E)-3,7-dimethyl-1,1-bis(2,2,2-trifluoroethoxy)octa-2,6-diene, (Z)-2-(2,6-dimethylhept-1-en-1-yl)-5,5-dimethyl-1,3-dioxane, (Z)-3,7-dimethyl-1,1-bis(2,2,2-trifluoro-ethoxy)oct-2-ene, (Z)-3,7-dimethyl-1,1-bis(2,2,2-trifluoroethoxy)octa-2,6-diene, 2,6-dimethyl-8,8-bis(2,2,2-trifluoroethoxy)oct-2-ene, (R)-2,6-dimethyl-8,8-bis(2,2,2-trifluoroethoxy)oct-2-ene, 2-((1Z,3E)-4,8-dimethylnona-1,3,7-trien-1-yl)-2,5,5-trimethyl-1,3-dioxane, 2-((1E,3Z)-4,8-dimethylnona-1,3,7-trien-1-yl)-2,5,5-trimethyl-1,3-dioxane, 2-((1Z,3Z)-4,8-dimethylnona-1,3,7-trien-1-yl)-2,5,5-trimethyl-1,3-dioxane, (6Z,8E)-2,6-dimethyl-10,10-bis(2,2,2-trifluoroethoxy)un-deca-2,6,8-triene, (6E,8Z)-2,6-dimethyl-10,10-bis(2,2,2-trifluoroethoxy)undeca-2,6,8-triene, (6Z,8Z)-2,6-dimethyl-10, 10-bis(2,2,2-trifluoroethoxy)undeca-2,6,8-triene, (Z)-2,5-dimethyl-2-(4,8,12-trimethyltridec-3-en-1-yl)-1,3-dioxane, (R,Z)-2,5-dimethyl-2-(4,8,12-trimethyltridec-3-en-1-yl)-1,3-dioxane, (Z)-6,10,14-trimethyl-2,2-bis(2,2,2-trifluoroethoxy)pentadec-5-ene, (R,Z)-6,10,14-trimethyl-2,2-bis(2,2,2-trifluoroethoxy)pentadec-5-ene.

In step a) a cis or a trans isomer of an unsaturated compound A is provided.

In one embodiment only one single stereoisomer of the compound A is provided. Such a single stereoisomer of compound A may be a result of a stereoselective synthesis or of a separation process of stereoisomers.

In another embodiment the cis or a trans isomer of a unsaturated compound A is provided as a mixture of cis and trans isomers in a non-equilibrium cis/trans ratio. Typically such a non-equilibrium cis/trans ratio is larger than 70/30, preferably larger than 80/20, more preferably larger than 90/10 or smaller than 30/70, preferably smaller than 20/80, more preferably smaller than 10/90.

Nitrogen Monoxide

In step b) nitrogen monoxide is added to the cis or trans isomer of the unsaturated compound A of step a);

Nitrogen monoxide is a cis/trans isomerization catalyst which isomerizes the carbon carbon double bond(s).

It is preferred that that nitrogen monoxide is introduced to unsaturated compound A at atmospheric pressure or up to 1 MPa over-pressure.

It is further preferred that nitrogen monoxide is introduced to unsaturated compound A at atmospheric pressure or up to 1 MPa over-pressure.

Nitrogen monoxide can be added in step b) as a gas mixture with at least one other gas, preferably an inert gas, most preferred with nitrogen.

It is preferred that the amount of nitrogen monoxide in the gas mixture is in the range of 10-60% by weight.

Nitrogen monoxide can be applied from a gas cylinder or can be prepared on spot, for example from $NaNO_2$ and $FeSO_4$ and sulphuric acid as described in the experimental part.

Isomerization

In step c) the mixture of nitrogen monoxide and cis or trans isomer of the unsaturated compound A is heated to a temperature of between 20° C. and the boiling point of the unsaturated compound A, particularly between 50° C. and the boiling point of the unsaturated compound A. In the present document the "boiling point of the unsaturated compound A" is defined as being the boiling point of the lowest boiling cis or trans isomers being formed by the process.

Under the action of nitrogen monoxide and temperature the cis and/or trans isomers of the unsaturated compound A isomerize. The ratio of cis and trans isomers being formed by the isomerization converges over time gradually to an equilibrium, e.g. the equilibrium cis/trans ratio. This equilibrium cis/trans ratio is a specific value which is different for each unsaturated compound A.

The isomerization of a cis or of a trans isomer of an unsaturated compound A is very interesting because very often one of the isomers is the isomer of interest. The cis and trans isomers mostly have different properties. For example core properties of interest such as odour or reactivity in specific chemical reactions is strongly different for the trans as compared to the cis isomer. In case of citral the trans isomer, geranial (=(E)-3,7-dimethylocta-2,6-dienal), has a strong lemon odour, whereas the cis isomer, neral (=(Z)-3,7-dimethylocta-2,6-dienal), has a lemon odour which is less intense, but sweeter. On the other hand if the unsaturated compound A has prochiral carbon-carbon double bond(s) the derivatization of this prochiral carbon-carbon double bond may lead to the formation of a chiral compound of a specific stereoisomeric configuration. For example an asymmetric hydrogenation of unsaturated compound A leads to the formation of stereogenic centre of the R or S configuration.

The isomerization offers the unique possibility of transforming at least a part of the undesired isomer into the desired isomer (=isomer of interest). On performing the method of isomerization and isolation in an optimal way, it even can be achieved that essentially all of the undesired isomer(s) can be transformed into the desired isomer(s) starting from a undesired isomer or a mixture of desired and undesired cis/trans isomers. More details for this possibility are given later in this document.

The above described process of a cis/trans isomerization of an unsaturated compound A leads to a mixture of cis/trans isomers of the unsaturated compound A.

From this mixture an isomer, the desired isomer, can be isolated. As the cis and trans isomers have different boiling points the favourite method of isolation is distillation. In order to minimize thermal degradation of the isomers it is advisable to distil under reduced pressure and by means of a distillation column. Very often the boiling points are very similar, however, by using specific distillation techniques and equipment it is nevertheless possible to separate or at least to enrich the desired isomer.

As not always the lowest boiling isomer is the one of interest there need to be principally two different processes of interest which are described in the following.

In case the lowest boiling isomer is the one of interest, in a further aspect the invention relates to a process of producing a specific cis isomer, respectively a specific trans isomer, of an unsaturated compound A being selected from the group consisting of unsaturated ketones, unsaturated ketals, unsaturated aldehydes, unsaturated acetals, unsaturated carboxylic acids, esters of an unsaturated carboxylic acid, amides of an unsaturated carboxylic acid and unsaturated alcohols from a mixture of cis and trans isomers thereof comprising the steps i) providing a mixture of cis isomer(s) in an amount of weight $w_{cis}$, and of trans isomer(s) in an amount of weight $w_{trans}$ of the unsaturated compound A;

ii) adding nitrogen monoxide iii) heating the mixture to a temperature $T_{iso1}$, which is the boiling point of that isomer $I_{lbp}$ which has the lowest boiling point of the mixture of the cis/trans isomers of step i);

iv) distilling off the isomer $I_{lbp}$ and collecting the isomer $I_{lbp}$;

v) cis/trans isomerization of the isomer(s) $I_{hbp}$ having a higher boiling point than the isomer $I_{lbp}$ in the presence of nitrogen monoxide being added in step ii);

wherein step ii) can take place before, during or after steps iii) and/or iv); and wherein after the step v) the steps ii) and iii) and iv) and v) are repeated subsequently and wherein the sum of the weight of all the collected isomer $I_{lbp}$ is more than $w_{cis}$ in case the collected isomer $I_{lbp}$ is a cis isomer of said unsaturated compound A;

or more than $w_{trans}$ in case the collected isomer $I_{lbp}$ is a trans isomer of said unsaturated compound A;

and wherein weight $w_{cis}$ and weight $w_{trans}$ are each 0 gram to 10 tons, with the proviso that the ratio of $w_{cis}$ and $w_{trans}$ is larger than 70/30 or smaller than 30/70 with the proviso that $w_{cis}$ and $w_{trans}$ are not both 0 grams.

In this process a mixture of cis isomer(s) in an amount of weight $w_{cis}$ and of trans isomer(s) in an amount of weight $w_{trans}$ of the unsaturated compound A is provided in step i). Because the weight $w_{cis}$ of the cis isomer(s) or the weight $w_{trans}$ of the trans isomer(s) is in the range of 0 grams to 10 tons with the proviso that not both $w_{cis}$ and $w_{trans}$ are 0 grams, a "mixture" in this context applies also to a single stereoisomer and not only to real isomer mixtures.

In a preferred embodiment both weight $w_{cis}$ and weight $w_{trans}$ are different from 0 grams, so that in the mixture provided in step i) the cis and trans isomer(s) of the unsaturated compound A are both physically present.

In this process the isomer of interest, i.e. the desired isomer, is the isomer $I_{lbp}$ which is the isomer having the lowest boiling point of the mixture of the cis/trans isomers provided in step i).

This isomer $I_{lbp}$ is isolated and separated by distillation and is collected in step iv).

In order to optimize purity, the distillation is made by using specific distillation techniques assuring that impurities by other isomers are as little as possible. This particularly is also achieved in that only a part, namely the purest fractions, of the desired isomer is collected in a distillation whereas a remainder is left in the distillation flask In order to optimize the yield of the desired isomer, the isomer(s) $I_{hbp}$ having a higher boiling point than the isomer $I_{lbp}$ are cis/trans isomerized in the presence of nitrogen monoxide (being added in step ii) in step v).

In the case, which is even the preferred case, where only a part of the isomer(s) $I_{lbp}$ are distilled and collected in step iv) the remainder of the distillation comprises still isomer(s) $I_{lbp}$. In this case, in step v) the cis/trans isomerization is carried out on the remainder of the distillation.

The isomer(s) $I_{hbp}$ and/or the remainder of the distillation is either isomerized continuously or batchwise in the presence of nitrogen monoxide As by removal of the desired product the remainder of the distillation is enriched in the undesired isomer to a non-equilibrium cis/trans ratio, the system adjusts according to Le Chatelier's principle and searches to achieve the equilibrium cis/trans ratio by transforming (i.e. isomerizing) the non-desired isomer into the desired isomer facilitated by nitrogen monoxide, the cis/trans isomerization catalyst. By repeating the steps iii) and iv) and v) after step v) subsequently it is assured that the yield is increased. The overall yield of the desired isomer $I_{lbp}$ is heavily depending on the number of repetitions and/or the separation efficiency of the distillation.

The process leads to a net transformation of the undesired isomer to the desired isomer, which means in other words, that the weight of the collected isomer $I_{lbp}$ is more than $w_{cis}$ in case the collected isomer $I_{lbp}$ is a cis isomer of said unsaturated compound A;

or is more than $w_{trans}$ in case the collected isomer $I_{lbp}$ is a trans isomer of said unsaturated compound A;

when in the original mixture of cis and trans isomers of the unsaturated compound A provided in step a) the cis isomer(s) has a weight $w_{cis}$ and the trans isomer(s) has a weight $w_{trans}$.

As discussed, principally essentially all of the undesired isomer can be transformed into the desired isomer.

Hence, it is preferred that the weight of the collected isomer $I_{lbp}$ isomer is more than 80% by weight, preferably more than 90% by weight, of the sum of $w_{trans}$ and $w_{cis}$.

In case the higher boiling isomer is the one of interest, in a further aspect the invention relates to a process of producing a specific cis isomer, respectively a specific trans isomer, of an unsaturated compound A being selected from the group consisting of unsaturated ketones, unsaturated ketals, unsaturated aldehydes, unsaturated acetals, unsaturated carboxylic acids, esters of an unsaturated carboxylic acid, amides of an unsaturated carboxylic acid and unsaturated alcohols from a mixture of cis and trans isomers thereof comprising the steps a) providing a mixture of cis isomer(s) in an amount of weight $w_{cis}$ and of trans isomer(s) in an amount of weight $w_{trans}$ of the unsaturated compound A;

b) adding nitrogen monoxide c) heating the mixture to a temperature $T_{iso1}$, which is the boiling point of that isomer $I_{lbp}$ which has the lowest boiling point of the mixture of the cis/trans isomers of step a);

d) distilling off the isomer $I_{lbp}$ e) isolating the specific isomer $I_{hbp}$ which has a higher boiling point than the isomer $I_{lbp}$ from the remainder of step d) and collecting the isomer $I_{hbp}$;

f) cis/trans isomerization of the isomer(s) $I_{lbp}$ and the remainder of remainder of step e) in case there is a remainder after step e) in the presence of nitrogen monoxide being added in step b);

wherein step b) can take place before, during or after steps c) and/or f); and wherein after the step f) the steps b) and c) and d) and e) and f) are repeated subsequently and wherein the weight of the collected isomer $I_{hbp}$ is more than $w_{cis}$ in case the collected isomer $I_{hbp}$ is a cis isomer of said unsaturated compound A;

or more than $w_{trans}$ in case the collected isomer $I_{hbp}$ is a trans isomer of said unsaturated compound A;

and wherein weight $w_{cis}$ and weight $w_{trans}$ are each 0 gram to 10 tons, with the proviso that the ratio of $w_{cis}$ and $w_{trans}$ is larger than 70/30 or smaller than 30/70 with the proviso that $w_{cis}$ and $w_{trans}$ are not both 0 grams.

In this process a mixture of cis isomer(s) in an amount of weight $w_{cis}$ and of trans isomer(s) in an amount of weight $w_{trans}$ of the unsaturated compound A is provided in step a). Because the weight $w_{cis}$ of the cis isomer(s) or the weight of the $w_{trans}$ of the trans isomer(s) is in the range of 0 grams to 10 tons with the proviso that not both $w_{cis}$ and $w_{trans}$ are 0 grams, a "mixture" in this context applies also to a single stereoisomer and not only to real isomer mixtures.

In a preferred embodiment both weight $w_{cis}$ and weight $w_{trans}$ are different from 0 grams, so that in the mixture provided in step a) the cis and trans isomer(s) of the unsaturated compound A are both physically present.

In this process the isomer of interest, i.e. the desired isomer $I_{hbp}$ which has a higher boiling point than the isomer $I_{lbp}$ which is the isomer having the lowest boiling point of the mixture of the cis/trans isomers provided in step a).

The lowest boiling isomer $I_{lbp}$ is distilled off in step d).

The specific isomer $I_{hbp}$ which has a higher boiling point than the isomer $I_{lbp}$ is isolated from the remainder of the distillation of step d) and is collected in step e).

Figure 1:
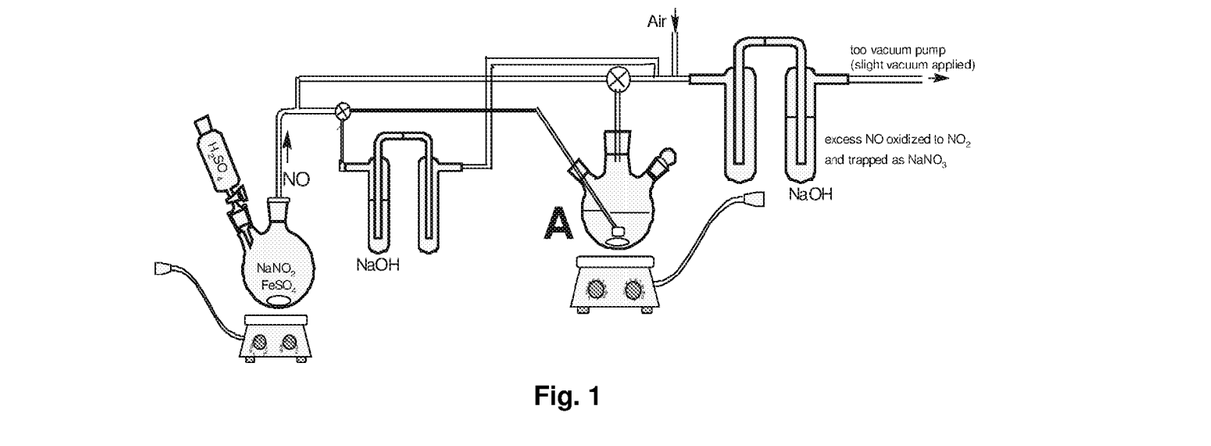
Figure 3:
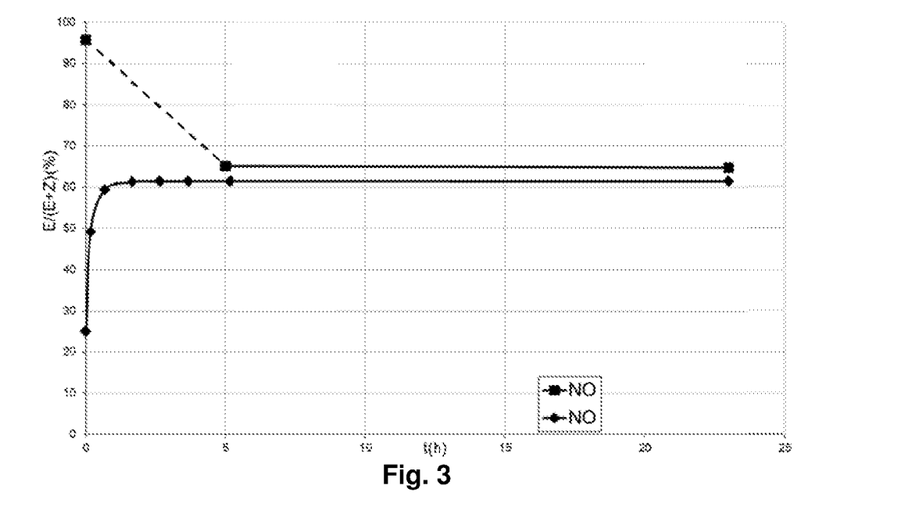

The isolation of the specific isomer $I_{hbp}$ is preferably done by specific distillation techniques, for example using a side take-off point at a rectification column and eventually further rectification of the material collected at said side take-off, such as the technique and equipment that has been disclosed for example in EP 2 269 998 A2, particularly FIGS. 1 and 3, the entire content of which is hereby incorporated by reference.

In order to optimize purity of the isomer $I_{hbp}$ the distillation in step d) and e) are made by using specific distillation techniques assuring that impurities by other isomers are as little as possible. This particularly is also achieved in that only a part, namely the purest fractions, of the desired isomer $I_{hbp}$ is collected in a distillation whereas the other fractions are combined with the remainder which is left in the distillation flask, and the lowest boiling isomer $I_{lbp}$ being distilled off in step d).

In step f) the isomer(s) $I_{lbp}$ and the remainder of step e) in case there is a remainder after step e) are isomerized in the presence of nitrogen monoxide being added in step b).

In the case, which is even the preferred case, where only a part of the isomer(s) $I_{hbp}$ are isolated and collected in step e) the remainder of the distillation comprises still isomer(s) $I_{hbp}$.

The isomer $I_{lbp}$ and the remainder of step e) are either isomerized continuously or batchwise in the presence of nitrogen monoxide. As by removal of desired product the remainder of the distillation is enriched in the undesired isomer to a non-equilibrium cis/trans ratio, the system adjusts according to Le Chatelier's principle and searches to achieve the equilibrium cis/trans ratio by transforming (i.e. isomerizing) the non-desired isomer into the desired isomer facilitated by nitrogen monoxide, the cis/trans isomerization catalyst. By repeating the steps steps c) and d) and e) and f) after step f) subsequently it is assured that the yield is increased. The overall yield of the desired isomer $I_{hbp}$ is heavily depending on the number of repetitions and/or the separation efficiency of the distillation.

The process leads to a net transformation of the undesired isomer to the desired isomer, which means in other words, that the weight of the collected isomer $I_{hbp}$ is more than $w_{cis}$ in case the collected isomer $I_{hbp}$ is a cis isomer of said unsaturated compound A;

or is more than $w_{trans}$ in case the collected isomer $I_{hbp}$ is a trans isomer of said unsaturated compound A;

when in the original mixture of cis and trans isomers of the unsaturated compound A provided in step a) the cis isomer(s) has a weight $w_{cis}$ and the trans isomer(s) has a weight $w_{trans}$.

As discussed, principally essentially all of the undesired isomer can be transformed into the desired isomer.

Hence, it is preferred that the weight of the collected isomer $I_{hbp}$ isomer is more than 80% by weight, preferably more than 90% by weight, of the sum of $w_{trans}$ and $w_{cis}$.

In both processes of producing a specific cis isomer, respectively a specific trans isomer, of an unsaturated compound A discussed in the previous paragraphs, it is preferred that nitrogen monoxide is introduced to unsaturated compound A at atmospheric pressure or up to 1 MPa overpressure.

In a further aspect the invention relates to compositions comprising nitrogen monoxide and an unsaturated compound A of the formula (I) or (II) or (IID) or (IIE).

Nitrogen monoxide and the unsaturated compound A of the formula (I) or (II) or (IID) or IIE) as well as their ratio and their preferred embodiments have been discussed already before in detail in this document.

In a further aspect the invention relates to a ketal or acetal which is selected from the group consisting of 2-(4,8-dimethylnona-3,7-dien-1-yl)-2,5,5-trimethyl-1,3-dioxane, 2,6-dimethyl-10,10-bis(2,2,2-trifluoroethoxy)undeca-2,6-diene, 2-(4,8-dimethylnon-3-en-1-yl)-2,5,5-trimethyl-1,3-dioxane, 6,10-dimethyl-2,2-bis(2,2,2-trifluoroethoxy)undec-5-ene, 2,5,5-trimethyl-2-(4,8,12-trimethyltridec-3-en-1-yl)-1,3-dioxane, (R)-2,5,5-trimethyl-2-(4,8,12-trimethyltridec-3-en-1-yl)-1,3-dioxane, 6,10,14-trimethyl-2,2-bis(2,2,2-trifluoroethoxy)pentadec-5-ene, (R)-6,10,14-trimethyl-2,2-bis(2,2,2-trifluoroethoxy)pentadec-5-ene, 2,5,5-trimethyl-2-(4,8,12-trimethyltrideca-3,7,11-trien-1-yl)-1,3-dioxane, 2,6,10-trimethyl-14,14-bis(2,2,2-trifluoroethoxy)pentadeca-2,6,10-triene, 2,5,5-trimethyl-2-(4,8,12-tri-methyltrideca-3,7-dien-1-yl)-1,3-dioxane, 6,10,14-trimethyl-2,2-bis(2,2,2-trifluoro-ethoxy)pentadeca-5,9-diene, 2-(2,6-dimethylhept-1-en-1-yl)-5,5-dimethyl-1,3-dioxane, 3,7-dimethyl-1,1-bis(2,2,2-trifluoroethoxy)oct-2-ene, 3,7-dimethyl-1,1-bis(2,2,2-trifluoroethoxy)octa-2,6-diene, 2,6-dimethyl-8,8-bis(2,2,2-trifluoroethoxy)-oct-2-ene, (R)-2,6-dimethyl-8,8-bis(2,2,2-trifluoroethoxy)oct-2-ene, 2-(4,8-di-methylnona-1,3,7-trien-1-yl)-2,5,5-trimethyl-1,3-dioxane, 2,6-dimethyl-10,10-bis(2,2,2-trifluoroethoxy)undeca-2,6,8-triene, 2,5-dimethyl-2-(4,8,12-trimethyltridec-3-en-1-yl)-1,3-dioxane, (R)-2,5-dimethyl-2-(4,8,12-trimethyltridec-3-en-1-yl)-1,3-dioxane, 6,10,14-trimethyl-2,2-bis(2,2,2-trifluoroethoxy)pentadec-5-ene and (R)-6,10,14-trimethyl-2,2-bis(2,2,2-trifluoroethoxy)pentadec-5-ene as well as all their possible E/Z-isomers.

These ketals and acetals are particularly suited for being isomerized according to the process of the invention.

Finally, in a further aspect the invention relates to the use of nitrogen monoxide as catalyst for the cis/trans isomerization of an unsaturated compound A which is selected from the group consisting of unsaturated ketones, unsaturated ketals, unsaturated aldehydes, unsaturated acetals, unsaturated carboxylic acids, esters of an unsaturated carboxylic acid and amides of an unsaturated carboxylic acid. This use has been discussed already before in this document in detail.

EXAMPLES

The present invention is further illustrated by the following experiments.

Production of NO and Isomerization Experiment

Nitrogen monoxide has been produced as shown in FIG. 1. Under and argon atmosphere, 5.86 g aqueous sulfuric acid (20%) (12.0 mmol) was cautiously dropped over 10 minutes and under stirring into a flask containing a solution of 0.86 g $NaNO_2$ (12.1 mmol) and 3.12 g $FeSO_4.7H_2O$ (11.2 mmol) in water (5 mL). The amounts of sulfuric acid, $NaNO_2$ and $FeSO_4$ have been calculated in such a way that 250 mL of NO gas (43 mol %) were produced. A constant stream of nitrogen monoxide was developed and bubbled into a flask containing the unsaturated compound A (25.6 mmol) to be isomerized over 10 minutes and under stirring. Nitrogen monoxide leaving the reaction flask was diluted with air and washed with NaOH solution. Afterwards the solution was stirred at room temperature for the time indicated.

In a first series of experiments the isomers of 6,10-dimethylundeca-5,9-dien-2-one have been separated by distillation. The E-isomer has been isolated as having a content of (E)-6,10-dimethylundeca-5,9-dien-2-one of 99.5% (determined by GC) and the Z-isomer has been isolated in an enriched fraction having a content of (Z)-6,10-dimethylundeca-5,9-dien-2-one of 76.5% and a content of (E)-6,10-dimethylundeca-5,9-dien-2-one of 21.4% (total 99.5% isomers, determined by GC).

Then the substance was isomerized by NO as described. The amount of E and Z isomers was measured by GC regularly after certain reaction times.

Figure 2:
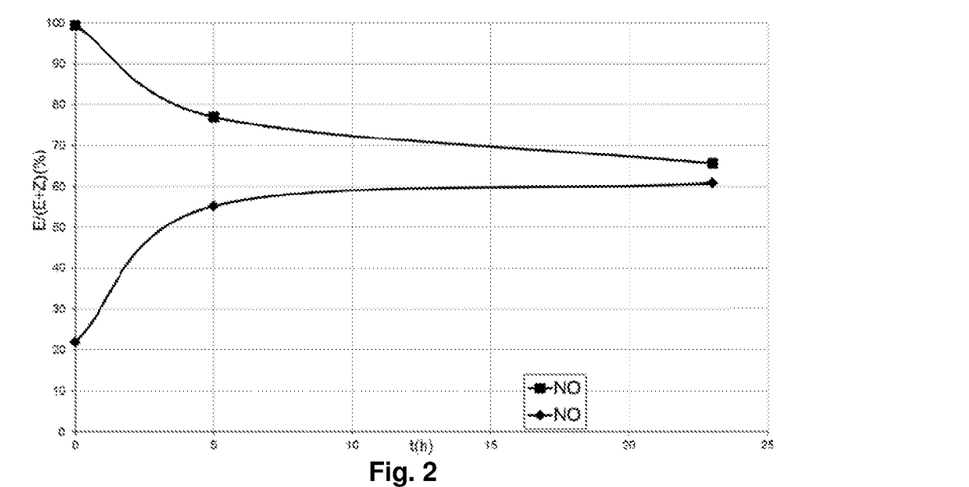

FIG. 2) shows the result of these isomerization experiments. The x-axis represents the time of reaction and the y-axis represents the percentage of E-isomer of the sum of isomers (E/(E+Z)) measured in the sample. For example a E/(E+Z) value of 80% represents a E/Z ratio of 80:20.

FIG. 2) shows that the equilibrium cis/trans ratio of 6,10-dimethylundeca-5,9-dien-2-one is between 60 and 65% E/(E+Z).

In a second series of experiments the isomers of 6,10-dimethylundec-5-en-2-one have been separated by distillation. The E-isomer has been isolated as having a content of (E)-6,10-dimethylundec-5-en-2-one of 95.5% (determined by GC) and the Z-isomer has been isolated in an enriched fraction having a content of (Z)-6,10-dimethylundec-5-en-2-one of 74.3% and a content of (E)-6,10-dimethylundeca-5,9-dien-2-one of 24.8% (total 99.2% isomers, determined by GC).

Then the substance was isomerized by NO as described. The amount of the individual isomers was measured by GC regularly after certain reaction times.

FIG. 3) shows the result of these isomerization experiments. The x-axis represents the time of isomerization, and the y-axis represents the percentage of E-isomer of the sum of isomers (E/(E+Z)) measured in the sample. For example a E/(E+Z) value of 80% represents a E/Z ratio of 80:20. The experiments show that NO is a very efficient isomerization catalyst. In the isomerization of the E isomer there have not been measured as many points as for Z, leading to impression that the E isomer would be slower isomerized (see dashed line), however, this is just due to the linear interpolation between the two points. FIG. 3) illustrates further that the equilibrium cis/trans ratio of 6,10-dimethylundec-5-en-2-one is at about 65% E/(E+Z).

In a third series of experiments the isomers of 3,7,11-trimethyl-1,6,10-dodecatrien-3-ol have been separated by distillation. The E-isomer has been isolated as having a content of (E)-3,7,11-trimethyl-1,6,10-dodecatrien-3-ol of 99.5% (determined by GC) and the Z-isomer has a content of (Z)-3,7,11-trimethyl-1,6,10-dodecatrien-3-ol of 99.7% (determined by GC).

Then the substance was isomerized by NO as described. The amount of the individual isomers was measured by GC regularly after certain reaction times.

Figure 4:
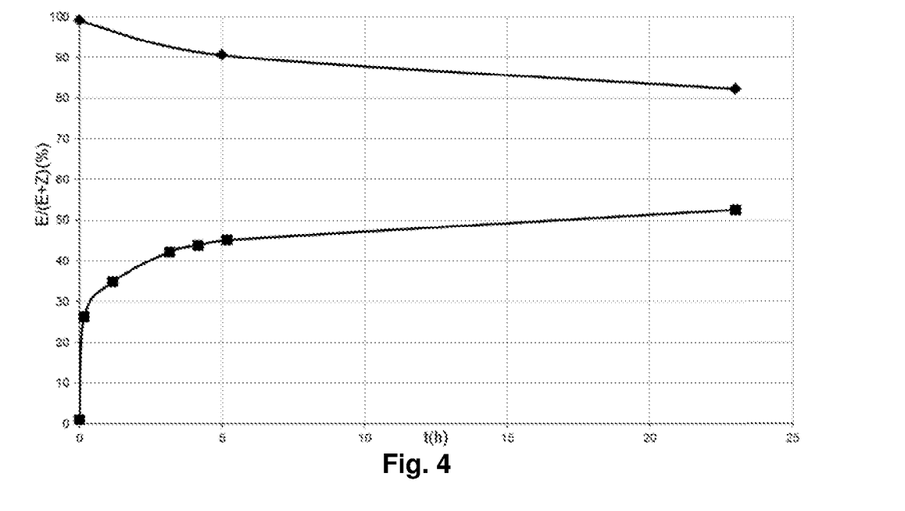

FIG. 4) shows the result of these isomerization experiments. The x-axis represents the time of isomerization, and the y-axis represents the percentage of E-isomer of the sum of isomers (E/(E+Z)) measured in the sample. For example a E/(E+Z) value of 80% represents a E/Z ratio of 80:20. The experiments show that NO is a fast isomerization catalyst. FIG. 4) illustrates further that the equilibrium cis/trans ratio of 3,7,11-trimethyl-1,6,10-dodecatrien-3-ol is between 52 and 82% E/(E+Z).

In a fourth series of experiments the isomers of 6,10,14-trimethylpentadeca-5,9,13-trien-2-one have been separated by distillation. The EE-isomer has been isolated as having a content of 99.5% of (5E,9E)-6,10,14-trimethylpentadeca-5,9,13-trien-2-one, 0% (5Z,9Z)-6,10,14-trimethylpentadeca-5,9,13-trien-2-one and 0.5% of the sum of (5E,9Z)- and (5Z,9E)-6,10,14-trimethylpentadeca-5,9,13-trien-2-one (total of 98.4% 6,10,14-trimethylpentadeca-5,9,13-trien-2-one isomers, measured by GC).

Then the substance was isomerized by NO as described. The amount of the individual isomers was measured by GC regularly after certain reaction times.

Figure 5A:
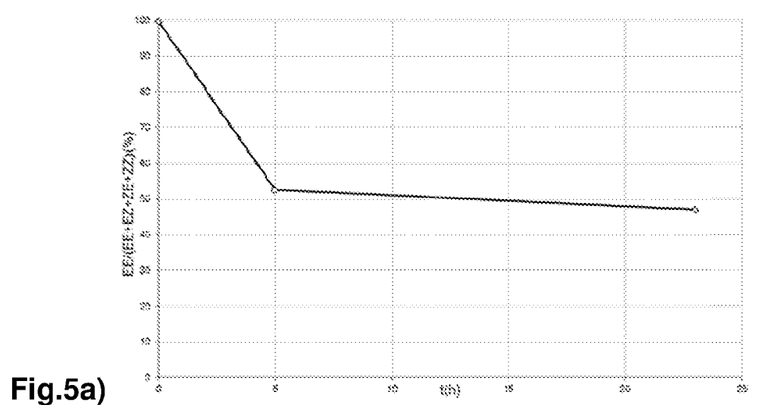
Figure 5B:
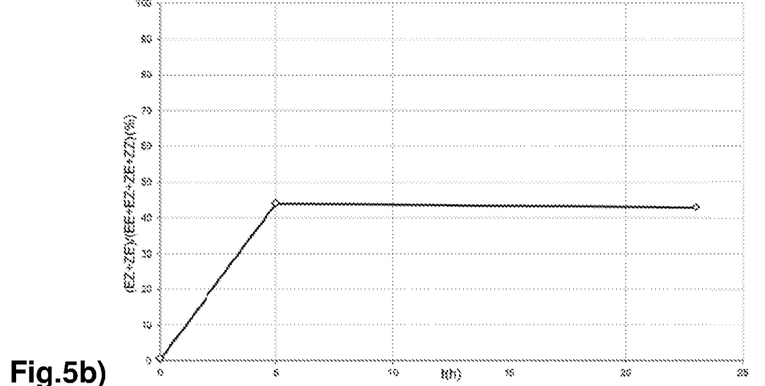
Figure 5C:
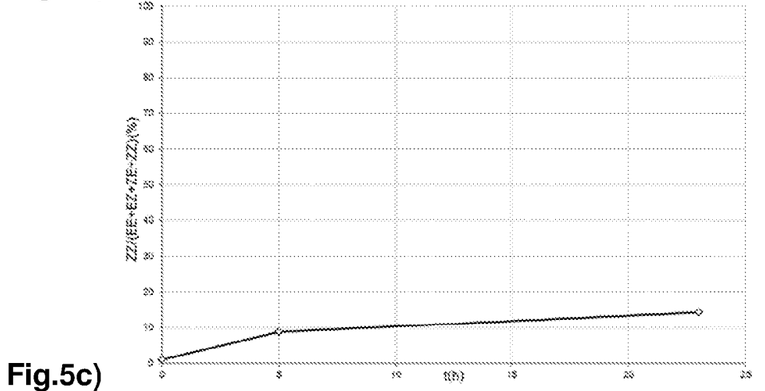

FIGS. 5a)-c) show the result of this isomerization experiment. The x-axis represents the time of isomerization, and the y-axis represents in FIG. 5a) the weight ratio of EE/(ZZ+EZ+ZZ+EE). The y-axis represents in FIG. 5b) the weight ratio of (EZ+ZE)/(ZZ+EZ+ZZ+EE). The y-axis represents in FIG. 5c) the weight ratio of ZZ/(ZZ+EZ+ZZ+EE). FIGS. 5a)-c) show that all isomers are isomerized furnishing a ratio of isomers of about 50% EE/(ZZ+EZ+ZE+EE), about 45% (EZ+ZE)/(ZZ+EZ+ZE+EE) and about 15% ZZ/(ZZ+EZ+ZE+EE).

In a fifth series of experiments the isomers of 6,10,14-trimethylpentadeca-5,9-dien-2-one have been separated by distillation. The mixture of EZ- and ZE-isomers has been isolated as having a content of 93.3% of the sum of (5E,9Z)- and (5Z,9E)-6,10,14-trimethylpentadeca-5,9-dien-2-one, 3.0% (5E,9E)-6,10,14-trimethylpentadeca-5,9-dien-2-one and 1.0% of (5Z,9Z)-6,10,14-trimethylpentadeca-5,9-dien-2-one (total of 97.3% 6,10,14-trimethylpentadeca-5,9-dien-2-one isomers, measured by GC).

Then the substance was isomerized by NO as described. The amount of the individual isomers was measured by GC regularly after certain reaction times.

Figure 6A:
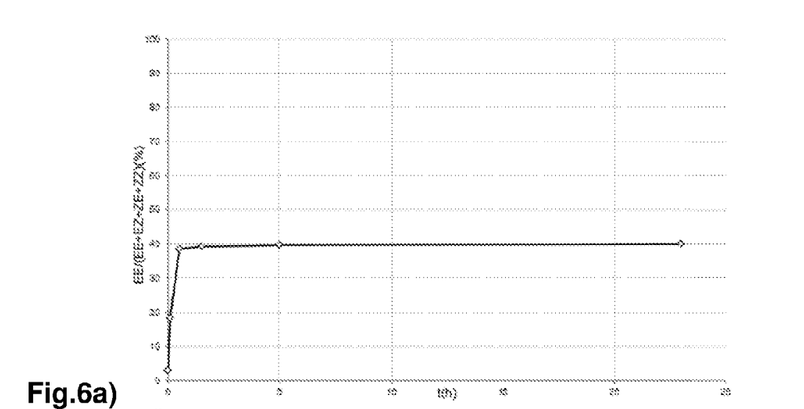
Figure 6B:
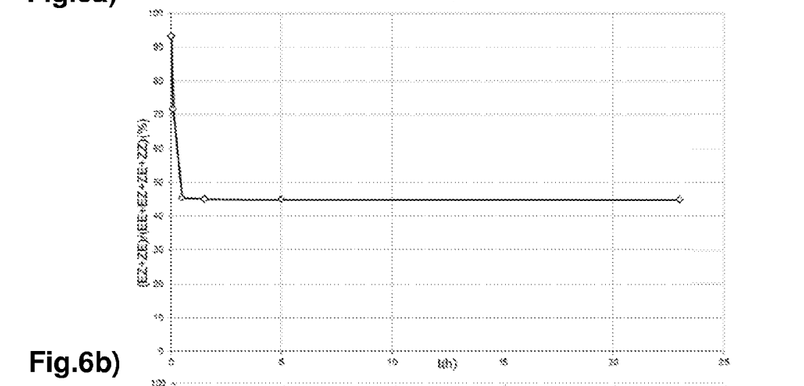
Figure 6C:
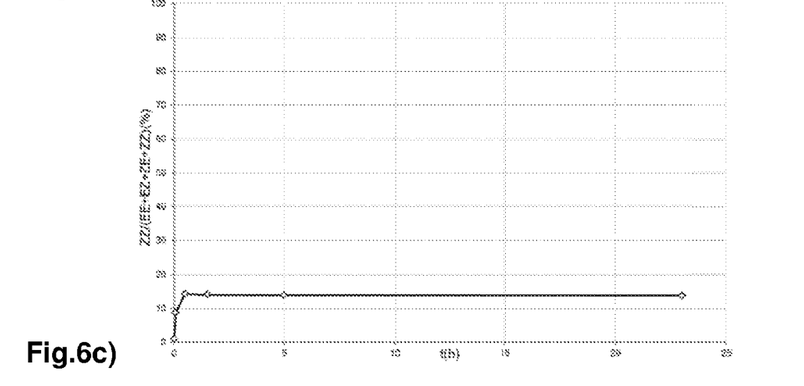

FIGS. 6a)-c) show the result of this isomerization experiment. The x-axis represents the time isomerization, and the y-axis represents in FIG. 6a) the weight ratio of EE/(ZZ+EZ+ZZ+EE). The y-axis represents in FIG. 6b) the weight ratio of (EZ+ZE)/(ZZ+EZ+ZZ+EE). The y-axis represents in FIG. 6c) the weight ratio of ZZ/(ZZ+EZ+ZZ+EE). FIGS. 6a)-c) show that all isomers are isomerized and an equilibrium is approached at about 15% ZZ/(ZZ+EZ+ZZ+EE), about 45% (EZ+ZE)/(ZZ+EZ+ZZ+EE) and about 40% EE/(ZZ+EZ+ZZ+EE).

The invention claimed is:

1. A process of a cis/trans isomerization of an unsaturated compound A having at least one but not more than two conjugated carbon-carbon double bonds, the compound A being selected from the group consisting of unsaturated ketones, unsaturated ketals, unsaturated aldehydes, unsaturated acetals, unsaturated carboxylic acids, esters of an unsaturated carboxylic acid, amides of an unsaturated carboxylic acid and unsaturated alcohols, wherein the process comprises the steps of:
 a) providing a cis or a trans isomer of the unsaturated compound A;
 b) adding nitrogen monoxide to the cis or trans isomer of the unsaturated compound A of step a) to form a mixture thereof;
 c) heating the mixture of nitrogen monoxide and cis or trans isomer of the unsaturated compound A to a temperature of between 10° C. and the boiling point of the unsaturated compound A, thereby leading to a mixture of cis/trans isomers of the unsaturated compound A.

2. The process according to claim 1, wherein the unsaturated compound A is an unsaturated ketone, an unsaturated ketal, an unsaturated aldehyde, an unsaturated acetal or an unsaturated alcohol.

3. The process according to claim 1, wherein step b) comprises including nitrogen monoxide to the cis or trans isomer of the unsaturated compound A at atmospheric pressure or up to 1 MPa over-pressure.

4. The process according to claim 3, wherein the over-pressure is from 10 to 300 kPa.

5. The process according to claim 1, wherein step b) comprises adding nitrogen monoxide as a gas mixture with at least one other gas.

6. The process according to claim 5, wherein the amount of nitrogen monoxide in the gas mixture is in the range of 10-60% by weight.

7. The process according to claim 1, wherein the unsaturated compound A is of formula (I), (II), (IID) or (IIE):

wherein Q stands for H or $CH_3$ and m and p stand independently from each other for a value of 0 to 3 with the proviso that the sum of m and p is 0 to 3; and wherein a wavy line represents a carbon-carbon bond which is linked to the adjacent carbon-carbon double bond so as to have said carbon-carbon double either in the Z or in the E-configuration, and wherein the substructures in formula (I), (II), (IID) and (IIE) represented by s1 and s2 can be in any sequence; and wherein the double bond having dotted lines ( ===== ) in formula (I), (II), (IID) and (IIE) represent either a single carbon-carbon bond or a double carbon-carbon bond; and wherein the symbol ✧ represents a stereogenic centre.

8. A process of producing a respective specific cis or trans isomer of an unsaturated compound A having at least one but not more than two conjugated carbon-carbon double bonds, the compound A being selected from the group consisting of unsaturated ketones, unsaturated ketals, unsaturated aldehydes, unsaturated acetals, unsaturated carboxylic acids, esters of an unsaturated carboxylic acid, amides of an unsaturated carboxylic acid and unsaturated alcohols from a mixture of cis and trans isomers thereof, wherein the process comprises the steps of:

i) providing a mixture of cis isomers in an amount of weight $w_{cis}$ and trans isomers in an amount of weight $w_{trans}$ of the unsaturated compound A;

ii) adding nitrogen monoxide to the mixture of cis and trans isomers provided by step i);

iii) heating the mixture of the nitrogen monoxide and cis and trans isomers obtained from step ii) to a temperature $T_{iso1}$, which is the boiling point of the isomer $I_{lbp}$ having a lowest boiling point of the mixture of the cis/trans isomers of step i);

iv) distilling off the isomer $I_{lbp}$ and collecting the isomer $I_{lbp}$;

v) conducting cis/trans isomerization of the isomer $I_{lbp}$ having a higher boiling point than the isomer $I_{lbp}$ in the presence of nitrogen monoxide being added in step ii); wherein step ii) can take place before, during or after steps iii) and/or iv); and wherein after the step v), the steps ii) and iii) and iv) and v) are repeated subsequently; and wherein a sum of the weight of all the collected isomer $I_{lbp}$ is either (1) more than the weight $w_{cis}$ in the case the collected isomer $I_{lbp}$ is a cis isomer of said unsaturated compound A or (2) more than the weight $w_{trans}$ in the case the collected isomer $I_{lbp}$ is a trans isomer of the unsaturated compound A; and wherein the weight $w_{cis}$ and the weight $w_{trans}$ are each 0 grams to 10 tons, with the proviso that the ratio of $w_{cis}$ and $w_{trans}$ is larger than 70/30 or smaller than 30/70 with the proviso that $w_{cis}$ and $w_{trans}$ are not both 0 grams.

9. The process of claim 8, wherein the weight of the collected isomer $I_{lbp}$ is more than 80% by weight of the sum of the weight $w_{trans}$ and the weight $w_{cis}$.

10. A process of producing a respective specific cis or trans isomer of an unsaturated compound A having at least one but not more than two conjugated carbon-carbon double bonds, the compound A being selected from the group consisting of unsaturated ketones, unsaturated ketals, unsaturated aldehydes, unsaturated acetals, unsaturated carboxylic acids, esters of an unsaturated carboxylic acid, amides of an unsaturated carboxylic acid and unsaturated alcohols from a mixture of cis and trans isomers thereof, wherein the process comprises the steps of:

a) providing a mixture of cis isomers in an amount of weight $w_{cis}$ and trans isomers in an amount of weight $w_{trans}$ of the unsaturated compound A;

b) adding nitrogen monoxide to the mixture of cis and trans isomers provided by step i);

c) heating the mixture of the nitrogen monoxide and cis and trans isomers obtained from step ii) to a temperature $T_{iso1}$, which is the boiling point of the isomer $I_{lbp}$ having a lowest boiling point of the mixture of the cis/trans isomers of step a);

d) distilling off the isomer $I_{lbp}$;

e) isolating the specific isomer $I_{hbp}$ which has a higher boiling point than the isomer $I_{lbp}$ from a remainder of step d) and collecting the isomer $I_{hbp}$;

f) conducting cis/trans isomerization of the isomer $I_{hbp}$ and a remainder of step e), if any, in the presence of nitrogen monoxide being added in step b); wherein step b) can take place before, during or after steps c) and/or f); and wherein after the step f), the steps b) and c) and d) and e) and f) are repeated subsequently, and wherein the weight of the collected isomer $I_{hbp}$ is either (1) more than the weight $w_{cis}$ in the case the collected isomer $I_{hbp}$ is a cis isomer of the unsaturated compound A or (2) more than the weight $w_{trans}$ in the case the collected isomer $I_{hbp}$ is a trans isomer of said unsaturated compound A; and wherein the weight $w_{cis}$ and the weight $w_{trans}$ are each 0 grams to 10 tons, with the proviso that the ratio of $w_{cis}$ and $w_{trans}$ is larger than 70/30 or smaller than 30/70 with the proviso that $w_{cis}$ and $w_{trans}$ are not both 0 grams.

11. The process according to claim 8, wherein step b) comprises introducing nitrogen monoxide to the mixture of cis and trans isomers of the unsaturated compound A at atmospheric pressure or up to 1 MPa over-pressure.

12. The process according to claim 5, wherein the at least one other gas is an inert gas.

13. The process according to claim 12, wherein the inert gas is nitrogen.

14. The process of claim 9, wherein the weight of the collected isomer $I_{lbp}$ is more than 90% by weight of the sum of the weight $w_{trans}$ and the weight $w_{cis}$.

15. A composition comprising:
(a) nitrogen monoxide; and
(b) an unsaturated compound A of the formula (I), (II), (IID) or (IIE):

wherein Q stands for H or $CH_3$ and m and p stand independently from each other for a value of 0 to 3 with the proviso that the sum of m and p is 0 to 3; and wherein a wavy line represents a carbon-carbon bond which is linked to the adjacent carbon-carbon double bond so as to have said carbon-carbon double either in the Z or in the E-configuration, and wherein the substructures in formula (I), (II), (IID) and (IIE) represented by s1 and s2 can be in any sequence; and wherein the double bond having dotted lines ( ===== ) in formula (I), (II), (IID) and (IIE) represent either a single carbon-carbon bond or a double carbon-carbon bond; and wherein the symbol ✧ represents a stereogenic centre.

16. A ketal or acetal which is selected from the group consisting of 2-(4,8-dimethylnona-3,7-dien-1-yl)-2,5,5-trimethyl-1,3-dioxane, 2,6-dimethyl-10,10-bis(2,2,2-trifluoroethoxy)undeca-2,6-diene, 2-(4,8-dimethylnon-3-en-1-yl)-2,5,5-trimethyl-1,3-dioxane, 6,10-dimethyl-2,2-bis(2,2,2-trifluoro-ethoxy)undec-5-ene, 2,5,5-trimethyl-2-(4,8,12-trimethyltridec-3-en-1-yl)-1,3-dioxane, (R)-2,5,5-trimethyl-2-(4,8,12-trimethyltridec-3-en-1-yl)-1,3-dioxane, 6,10,14-trimethyl-2,2-bis(2,2,2-trifluoroethoxy)pentadec-5-ene, (R)-6,10,14-trimethyl-2,2-bis(2,2,2-trifluoroethoxy) pentadec-5-ene, 2,5,5-trimethyl-2-(4,8,12trimethyltrideca-3,7,11-trien-1-yl)-1,3-dioxane, 2,6,10-trimethyl-14,14-bis(2,2,2-trifluoroethoxy)pentadeca-2,6,10-triene, 2,5,5-trimethyl-2-(4,8,12-tri-methyltrideca-3,7-dien-1-yl)-1,3-dioxane, 6,10,14-trimethyl-2,2-bis(2,2,2-trifluoroethoxy) pentadeca-5,9-diene, 2-(2,6-dimethylhept-1-en-1-yl)-5,5-dimethyl-1,3-dioxane, 3,7-dimethyl-1,1-bis(2,2,2-trifluoroethoxy)oct-2-ene, 3,7-dimethyl-1,1-bis(2,2,2-trifluoroethoxy)octa-2,6-diene, 2,6-dimethyl-8,8-bis(2,2,2-tri-fluoro-ethoxy)-oct-2-ene, (R)-2,6-dimethyl-8,8-bis(2,2,2-trifluoroethoxy)oct-2-ene, 2-(4,8-di-methylnona-1,3,7-trien-1-yl)-2,5,5-trimethyl-1,3-dioxane, 2,6-dimethyl-10,10-bis(2,2,2-trifluoroethoxy) undeca-2,6,8-triene, 2,5-dimethyl-2-(4,8,12-trimethyltridec-3-en-1-yl)-1,3-dioxane, (R)-2,5-dimethyl-2-(4,8,12-tri-methyltridec-3-en-1-yl)-1,3-dioxane, 6,10,14-trimethyl-2,2-bis(2,2,2-trifluoro-ethoxy)pentadec-5-ene and (R)-6,10,14-trimethyl-2,2-bis(2,2,2-trifluoro-ethoxy)pentadec-5-ene and all possible E/Z-isomers thereof.

17. A method for the cis/trans isomerization of an compound A having at least one but not more than two conjugated carbon-carbon double bonds, the compound A being selected from the group consisting of unsaturated ketones, unsaturated ketals, unsaturated aldehydes, unsaturated acetals, unsaturated carboxylic acids, esters of an unsaturated carboxylic acid and amides of an unsaturated carboxylic acid, wherein the method comprises subjecting the unsaturated compound A to cis/trans isomerization conditions in the presence of nitrogen monoxide as a catalyst.

* * * * *